United States Patent
Fox (10) Patent No.: US 7,310,190 B2
(45) Date of Patent: Dec. 18, 2007

(54) VEHICLE IMAGING SYSTEM WITH WINDSHIELD CONDITION DETERMINATION

(75) Inventor: Stephen H. Fox, Kokomo, IN (US)

(73) Assignee: Delphi Technologies, Inc., Troy, MI (US)

(*) Notice: Subject to any disclaimer, the term of this patent is extended or adjusted under 35 U.S.C. 154(b) by 0 days.

(21) Appl. No.: 11/351,010

(22) Filed: Feb. 9, 2006

(65) Prior Publication Data

US 2007/0182816 A1   Aug. 9, 2007

(51) Int. Cl.
G02B 1/06 (2006.01)
G02B 3/12 (2006.01)
G02B 27/10 (2006.01)

(52) U.S. Cl. .................................. 359/666; 359/618

(58) Field of Classification Search ........ 359/630–634, 359/618, 624, 676, 665, 666; 345/7–9; 348/115
See application file for complete search history.

(56) References Cited

U.S. PATENT DOCUMENTS

| | | | |
|---|---|---|---|
| 5,933,277 A | 8/1999 | Troxell et al. | |
| 5,953,161 A | 9/1999 | Troxell et al. | |
| 6,320,176 B1* | 11/2001 | Schofield et al. | 250/208.1 |
| 6,369,954 B1 | 4/2002 | Berge et al. | |
| 2004/0143380 A1* | 7/2004 | Stam et al. | 701/36 |
| 2005/0002113 A1 | 1/2005 | Berge | |
| 2005/0035926 A1* | 2/2005 | Takenaga et al. | 345/8 |
| 2005/0098712 A1* | 5/2005 | Stam et al. | 250/208.1 |
| 2006/0125919 A1* | 6/2006 | Camilleri et al. | 348/148 |

FOREIGN PATENT DOCUMENTS

| | | |
|---|---|---|
| WO | WO 99/18456 | 4/1999 |
| WO | WO 00/58763 | 10/2000 |

OTHER PUBLICATIONS

Blau, John, "Philips: Patent dispute looms over fluid lens," CIO, Mar., 2004, IDG Communications Ltd. (2 pgs.).
Harris, Siân, "Philips demonstrates fluid lens," optics.org, Mar., 2004, http://optics.org/articles/news (2 pgs.).
U.S. Appl. No. 10/919,163, filed Aug. 16, 2004, titled "Refractive Block and Imaging Systems".
U.S. Appl. No. 10/975,264, filed Oct. 28, 2004, titled "Actively-Illuminating Optical Sensing System for an Automobile".

* cited by examiner

*Primary Examiner*—Alicia M Harrington
(74) *Attorney, Agent, or Firm*—Jimmy L. Funke (57) ABSTRACT

An imaging system for use in a vehicle is disclosed wherein the imaging system images an object spaced apart from the vehicle in a first configuration and images an object supported by the vehicle in a second configuration. The imaging system may include a fluid lens. An imaging system for use in a vehicle is disclosed wherein the imaging system has a first configuration corresponding to a first imaging application and a second configuration corresponding to a second imaging application. The imaging system may include a fluid lens.

9 Claims, 7 Drawing Sheets

VEHICLE IMAGING SYSTEM WITH WINDSHIELD CONDITION DETERMINATION

TECHNICAL BACKGROUND

The present invention relates to an imaging system for use in a vehicle, in particular an imaging system including optics that permits the imaging system to image objects within the vehicle, a window of the vehicle, and objects spaced apart from the vehicle.

BACKGROUND OF THE INVENTION

Imaging systems are used with vehicles. Some imaging systems are located behind a window of the vehicle and image objects that are spaced apart from the vehicle. Exemplary imaging systems include lane tracking systems, lane departure warning systems, adaptive cruise control systems, night vision systems, frontal imaging systems, side imaging systems, rear imaging systems, collision warning systems, and pedestrian/cross traffic identification systems.

The condition or optical quality of the window through which the imaging system looks may impede the operation of the imaging system. For example, in the case of a forward looking vision system the optical quality of the windshield of the vehicle may be degraded by fog, frost, dirt, or other objects which cloud the scene or objects being imaged and lower the signal contrast of the image. Further, scratches, rock chips, and bird droppings cause obstructions that may cause false positive warnings, or inhibit correct identification of genuine targets. These conditions may disrupt the operation of the respective vision system and may lead to an indication that the vision system is not functioning properly when in reality only the optical quality of the window needs to be improved.

It is known to detect the presence of precipitation on a windshield of a vehicle by total internal reflection. A beam of light is reflected from the windshield at a particular angle. The presence of water on the windshield defeats this reflection causing a change in the intensity of light received at the detector. Further, it is known to include an LED in a camera housing whose emitted light is reflected off of the windshield. The pattern of the reflected light is evaluated to determine the windshield condition.

In addition to the optical quality of the windshield, forward-looking cameras are subject to reflections from the inside of the windshield. Objects placed on the dashboard appear in the field of view of the vision system through the partially reflecting property of the windshield. One solution to this problem has been placing a non-reflecting light shield underneath the optics of the imaging system to prevent such reflections from entering the imaging system. Such a shield is large and must be redesigned for each model automobile into which the imaging system is placed. Another solution has been the inclusion of a polarizing element to eliminate the typically polarized reflections from the windshield from entering the imaging system. However, such polarizer elements cut the detector sensitivity by half as they eliminate half of the incoming light and do not function well over the full range of incidence angles.

SUMMARY OF THE INVENTION

The present invention provides improved imaging systems for vehicles that monitor objects spaced apart from the vehicle, objects supported by the vehicle including a window of the vehicle, or both objects spaced apart from the vehicle and objects supported the vehicle.

In an exemplary embodiment of the present invention an imaging system for use with a vehicle is provided. The vehicle including a window through which light is transmitted. The imaging system comprising a detector which provides an image of the light transmitted through the window; imaging optics and a controller. The imaging optics having a first configuration wherein an object spaced apart from the vehicle is imaged onto the detector and a second configuration wherein at least a portion of the window is imaged onto the detector. The controller operably coupled to the imaging optics. The controller configured to adjust the imaging optics to place the imaging optics in the first configuration to image the object spaced apart from the vehicle and further configured to adjust the imaging optics to place the imaging optics in the second configuration to image the portion of the window.

In another exemplary embodiment of the present invention an imaging system for use with a vehicle is provided. The vehicle including a window through which light is transmitted. The imaging system comprising a detector which provides an image of the light transmitted through the window; imaging optics, and a controller. The imaging optics having a first configuration wherein a first object spaced apart from the vehicle is imaged onto the detector and a second configuration wherein a second object supported by the vehicle is imaged onto the detector. The controller operably coupled to the imaging optics. The controller configured to adjust the imaging optics to place the imaging optics in the first configuration to image the first object and further configured to adjust the imaging optics to place the imaging optics in the second configuration to image the second object.

In yet a further exemplary embodiment of the present invention an imaging system for use with a vehicle is provided. The vehicle including a window through which light is transmitted. The imaging system comprising a detector which provides an image of the light transmitted through the window; imaging optics; and a controller. The imaging optics including a variable focus lens positioned to focus light on the detector. The imaging optics having a first configuration corresponding to a first imaging application analyzing one or more objects spaced apart from the vehicle and having a second configuration corresponding to a second imaging application analyzing one or more objects spaced apart from the vehicle. The controller operably coupled to the variable focus lens. The controller configured to adjust a shape the variable focus lens, wherein the first imaging configuration corresponds to a first shape of the variable focus lens and the second imaging configuration corresponds to a second shape of the variable focus lens.

In still another exemplary embodiment of the present invention, a method for detecting problems with an imaging system for a vehicle is provided. The imaging system looking at a scene through a window of the vehicle. The method comprising the steps of identifying a degraded optical quality of the window with an optical system having a variable focus lens; and alerting a driver of the vehicle of the degraded optical quality of the window. In one example, the step of identifying the degraded optical quality of the window includes the steps of adjusting a focal length of a variable focus lens of an imaging system to image at least a portion of the window; and detecting an unacceptable condition of the window based on an analysis of an image of the window. In another example, the step of alerting the driver of the vehicle of the degraded optical quality of the window includes the step of providing an indication to a driver of the vehicle of the degraded optical quality of the window.

In a further exemplary embodiment of the present invention, a method for detecting problems with an imaging system for a vehicle is provided. The imaging system looking at a scene through a window of the vehicle. The method comprising the steps of: imaging the scene with the imaging system; adjusting the imaging system to image at least a portion of the window; imaging the at least a portion of the window; and analyzing the imaged portion of the window to detect if a degraded optical quality of the window is present.

BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. Although the drawings represent embodiments of the present invention, the drawings are not necessarily to scale and certain features may be exaggerated in order to better illustrate and explain the present invention. The exemplifications set out herein illustrate embodiments of the invention in several forms and such exemplification is not to be construed as limiting the scope of the invention in any manner.

DESCRIPTION OF INVENTION

The embodiments discussed below are not intended to be exhaustive or limit the invention to the precise forms disclosed in the following detailed description. Rather, the embodiments are chosen and described so that others skilled in the art may utilize their teachings.

Figure 1:
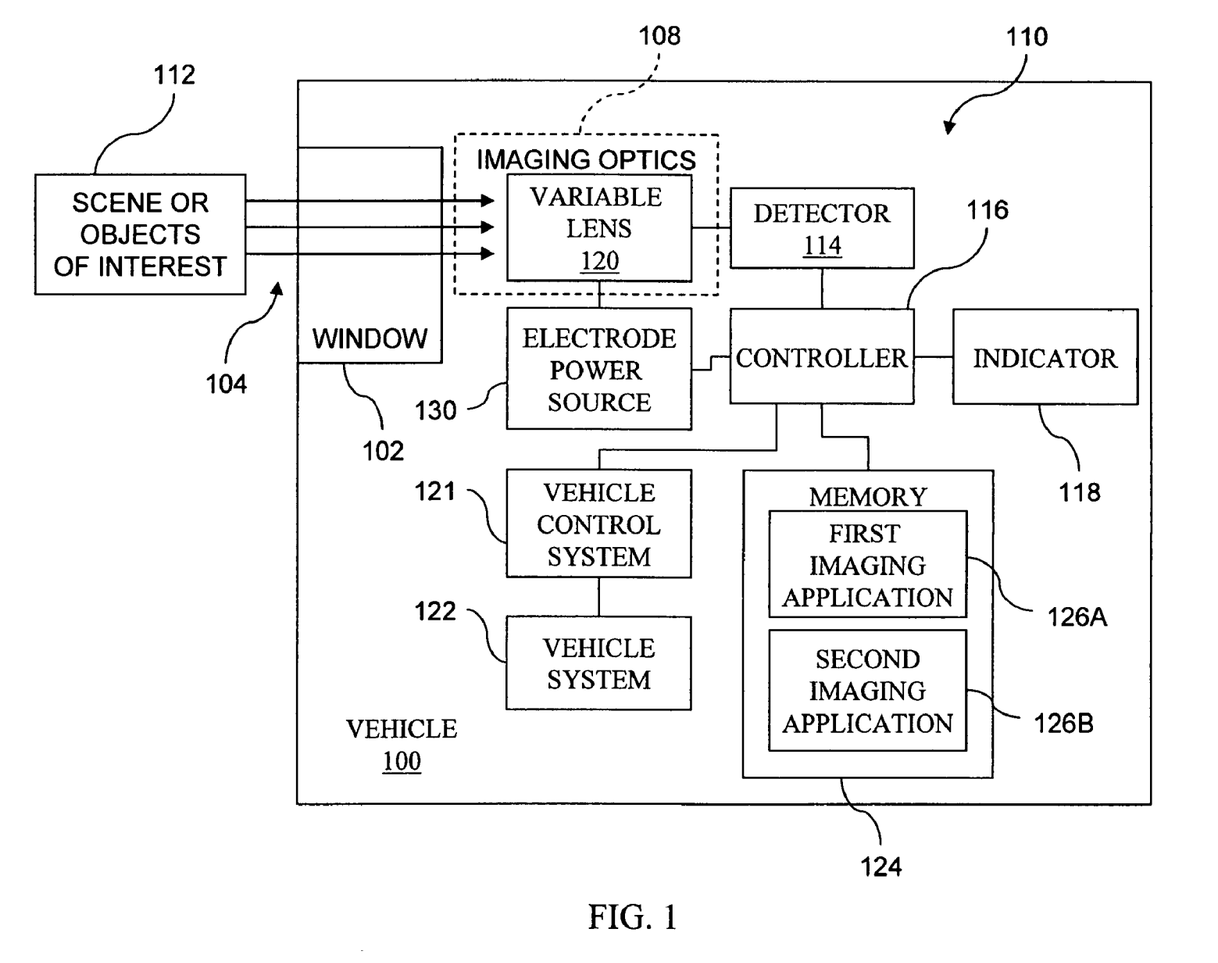
FIG. 1 is a representative diagram of a vehicle including a window and an imaging system which images objects or a scene of interest that is spaced apart from the vehicle.

Referring to FIG. 1, a vehicle 100 is shown. Exemplary vehicles include automobiles, trucks, airplanes, watercraft, and other exemplary motorized vehicles. Vehicle 100 includes a window 102. Exemplary windows include a front windshield, a rear windshield, one or more side windows, and any other suitable optically transparent regions that permit optical radiation 104, preferably visible light and/or non-visible light, such as infrared light, to enter an envelope of vehicle 100. The light 104 entering vehicle 100 is incident on imaging optics 108 of an imaging system 110. Imaging optics 108 form an image of a scene including one or more objects 112 on a detector 114 of imaging system 110. In one embodiment, detector 114 provides a digital image of the scene. Object 112 is shown spaced apart from vehicle 100. Exemplary objects include pedestrians, bicyclists, animals, trees, other vehicles, road signs, and any other object which may be positioned in the general vicinity of vehicle 100. In one embodiment, object 112 is spaced apart from imaging optics 108 from about 2 meters to about 150 meters. In another embodiment, object 112 is spaced apart from imaging optics 108 by at least about 2 meters. In another embodiment, imaging optics 108 are arranged to image objects within vehicle 100 such as passengers, eyes of driver, car seats, and other objects.

Imaging optics 108 may include multiple optical elements such as lens, mirrors, and prisms whose optical characteristics and spacing is selected based on the desired imaging application. In one embodiment, the relative location of the various optical elements is set. In one embodiment, imaging optics 108 includes a variable focus lens 120 whose focal length may be adjusted. In another embodiment, imaging optics 108 includes a variable focus lens 120 and one or more conventional optical elements each having a fixed focus, such as glass or plastic optics. In another embodiment, imaging optics 108 may include at least two variable focus lenses 120 and may include additional conventional optics.

Imaging system 110 further includes a controller 116 which is configured to analyze the images formed on detector 114 and to provide one or more indications to an occupant of vehicle 100, such as with an indicator 118. Exemplary indicators include, lights on an instrument panel, chimes, haptic, and other suitable indicators. Further, controller 116 is configured to provide input signals to a vehicle control system 121, such as a processor, an actuator, a motor, circuitry, and another suitable controller, which in turn controls the operation of the one or more vehicle systems 122 of vehicle 100, such as brakes, suspension, steering, air bags, restraints, and other components of vehicle 100. In one example, controller 116 in response to the detection of a potential collision provides an input to an occupant restraint control system which increases the tension of a restraint or seat belt.

Exemplary applications of imaging system 110 include lane tracking systems, lane departure warning systems, adaptive cruise control systems, night vision systems, frontal imaging systems, side imaging systems, rear imaging systems, collision warning systems, pedestrian/cross traffic identification systems, and other suitable systems which based on images monitor one or more objects spaced apart from vehicle 100. Exemplary imaging systems are disclosed in U.S. Pat. No. 5,933,277; U.S. Pat. No. 5,935,161; and U.S. patent application Ser. No. 10/919,163, filed Aug. 16, 2004, titled "Refractive Block and Imaging Systems," the disclosures of which are expressly incorporated by reference herein. Exemplary imaging systems also include systems which monitor objects within vehicle 100, such as the occupant position systems and driver gaze systems described in U.S. patent application Ser. No. 10/975,264, filed Oct. 28, 2004, titled "Actively-Illuminating Optical Sensing System for an Automobile," the disclosure of which is expressly incorporated by reference herein.

In the illustrated embodiment shown in FIG. 1, controller 116 has access to a computer readable medium, memory 124, which includes software that is executed by controller 116. In the illustrated embodiment, memory 124 includes software related to a first imaging application 126A and a second imaging application 126B. The optical requirements for imaging optics 108 typically vary from application to application. For instance, an exemplary lane departure warning application requires imaging optics 108 to have a field of view of about 45 degrees while an exemplary night vision application requires imaging optics 108 to have a field of view of about 24 degrees. Further, the exemplary night vision application requires higher resolution performance on axis than the exemplary lane departure warning application. Thus, integrating the optical requirements of both the exemplary lane departure application and the exemplary night vision application into the same fixed imaging optics compromises the performance of one application or the other.

The incorporation of multiple imaging applications 126A and 126B into imaging system 110 is possible without sacrificing the performance of either application because imaging optics 108 may be reconfigured to accommodate the optical requirements of each application. In the illustrated embodiment, imaging optics 108 includes variable lens 120 which has an adjustable focal length. By adjusting the focal length of variable lens 120 various parameters of imaging optics 108 may be adjusted such as the focal length of imaging optics 108, the depth of focus of imaging optics 108, the object range of imaging optics 108, the field of view of imaging optics 108, the resolution of imaging optics 108, and the magnification of imaging optics 108. In one embodiment, imaging optics 108 includes two or more variable lens 120 to achieve the adjustment of one or more of the above-mentioned optical parameters.

In one embodiment, a focal length of variable focus lens 120 is changed by changing a shape of variable focus lens 120. As such, a parameter of imaging optics 108 may be altered without adjusting the relative location of one or more components of imaging optics 108. In one embodiment, variable focus lens 120 is a liquid lens. An exemplary liquid lens includes two immiscible fluids contained within a cylindrical housing. The shape of the boundary between the two fluids changes in response to the application of a voltage to the conductive fluid. In the illustrated embodiment, the shape of variable focus lens 120 is adjusted by altering a voltage across variable focus lens 120, the voltage being applied through an electrode of a power source 130. Exemplary fluid lens include the FluidFocus fluid lens available from Philips Research located at Koninklijke Philips Electronics N.V. Groenewoudseweg 1 5621 BA, Eindhoven the Netherlands and a fluid lens available from Varioptic located at Batiment Tony Garnier—8 B Rue Hermann Frenkel 69007 Lyon France. Additional details about suitable fluid lens are provided in U.S. Pat. No. 6,369,954, Ser. No. 09/529,193, issued Apr. 9, 2002 to Berge et al; U.S. Published Application No. 2005/0002113A1, Ser. No. 10/812,307, filed Mar. 30, 2004; International Application No. WO 00/58763; and International Application No. WO 99/18456, the disclosures of which are expressly incorporated by reference herein.

The voltage applied to variable focus lens 120 may be adjusted by controller 116. As such, controller 116 may configure imaging optics 108 for a first application, such as a lane departure warning application, and then reconfigure imaging optics 108 for a second application, such as a night vision application by adjusting the voltage applied to variable focus lens 120. The configuration of imaging optics 108 may be altered by controller 116 on a demand basis such as the activation of a second imaging application, based on other conditions, such as failure of a given imaging application and driver intervention. Variable lens 120 permits the ability to change a parameter of imaging optics 108 without having to move the location of a component of imaging optics 108.

Figure 2:
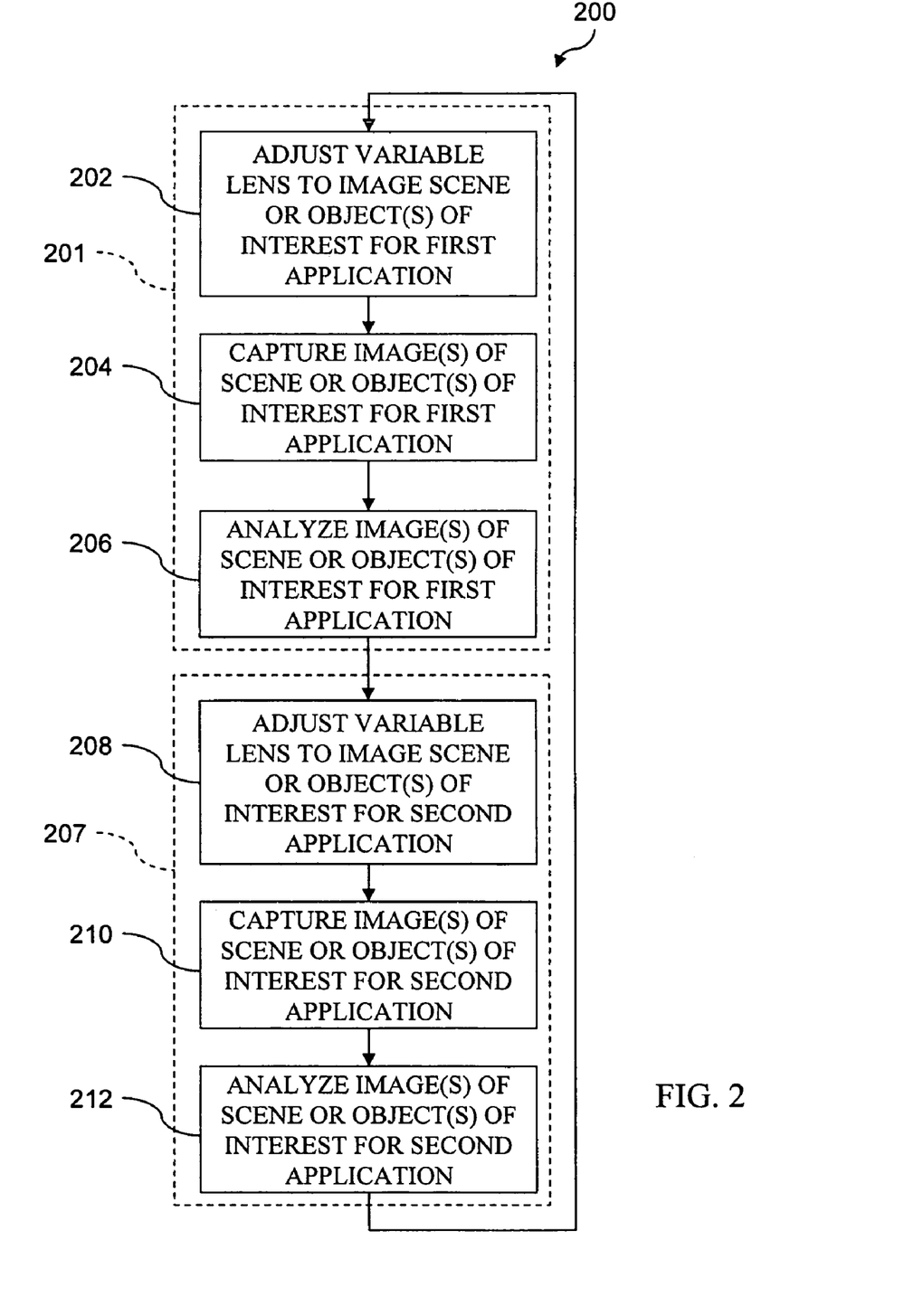
FIG. 2 is a flowchart of an exemplary method to be executed by the imaging system of FIG. 1.

In an exemplary embodiment, controller 116 is programmed to execute method 200 illustrated in FIG. 2. Controller 116 adjusts variable lens 120 to image a scene or objects of interest for first application 126A on detector 114, as represented by step 202. One or more images of the scene or objects of interest 112 for first application 126A are captured by controller 116, as represented by block 204. Controller 116 analyzes the captured one or more images for first application 126A, as represented by block 206. Further, after the completion of block 204, controller 116 adjusts variable lens 120 to image a scene or objects of interest 112 for a second application 126B on detector 114, as represented by step 208. One or more images of the scene or objects of interest 112 for second application 126B are captured by controller 116, as represented by block 210. Controller 116 analyzes the captured one or more images for second application 126B, as represented by block 212.

In one embodiment, controller 116 adjusts variable focus lens 120 and hence imaging optics 108 between each image frame captured with detector 114. Thus, although a single set of imaging optics 108 is used, each imaging application may have imaging optics 108 configured for that imaging application.

In one embodiment, imaging system 110 may perform a diagnosis of the condition or optical quality of window 102. Poor optical quality of window 102 may result in one or more of first application 126A and second application 126B not functioning properly and/or may degrade the usefulness of the images obtained by imaging system 110. For example, in the case of a forward looking vision system the optical quality of the windshield of vehicle 100 may be degraded by fog, frost, dirt, etc., which cloud the scene and lower the signal contrast. Further, scratches, rock chips, and bird droppings cause obstructions that may cause false positive warnings, or inhibit correct identification of genuine targets. These conditions may disrupt the operation of the respective imaging application 126 and may lead to an indication that imaging system 110 is not functioning properly when in reality only the optical quality of window 102 needs to be improved.

To diagnosis the optical quality of window 102, imaging optics 108 are adjusted to image at least a portion of window 102 on detector 114. Typically, when configured for use with one of first application 126A and second application 126B imaging optics 108 form an image of object(s) or scene 112 on detector 114. Objects or scene 112 is typically from about 2,000 millimeters (mm) to about 150,000 mm spaced apart from imaging optics 108 of vehicle 100. Assuming that imaging optics may be approximated as a thin lens system, then an image of object(s) or scene 112 is formed generally at the focus of imaging optics 108 in accordance with equation 1, $$\frac{1}{z_1} + \frac{1}{z_2} = \frac{1}{f} \quad (1)$$

wherein $z_1$ is the distance from object 112 to imaging optics 108, $z_2$ is the distance from imaging optics 108 to an image of object 112, and f is the focal length of imaging optics 108. Assuming that the focal length of imaging optics 108 is generally about 6 mm, then equation 1 may be reduced to equation 2.

$$\frac{1}{z_2} = \frac{1}{f} \qquad (2)$$

However, window 102 is typically about 5 mm to about 20 mm from imaging optics 108. Regarding the imaging of window 102, the term 1/z1 of equation 1 is not negligible as in the case of object 112 which is about 200 times to about 30,000 times further from imaging optics 108 than window 102. As such, assuming that detector 114 is about 8 mm from imaging optics 108 and the window 102 is about 20 mm from imaging optics the focal length of imaging optics 108 should be about 5.7 mm. Based on the typical focal length of 6 mm given above, the focal length of imaging optics 108 is reduced by about 5 percent to image window 102.

Figure 3:
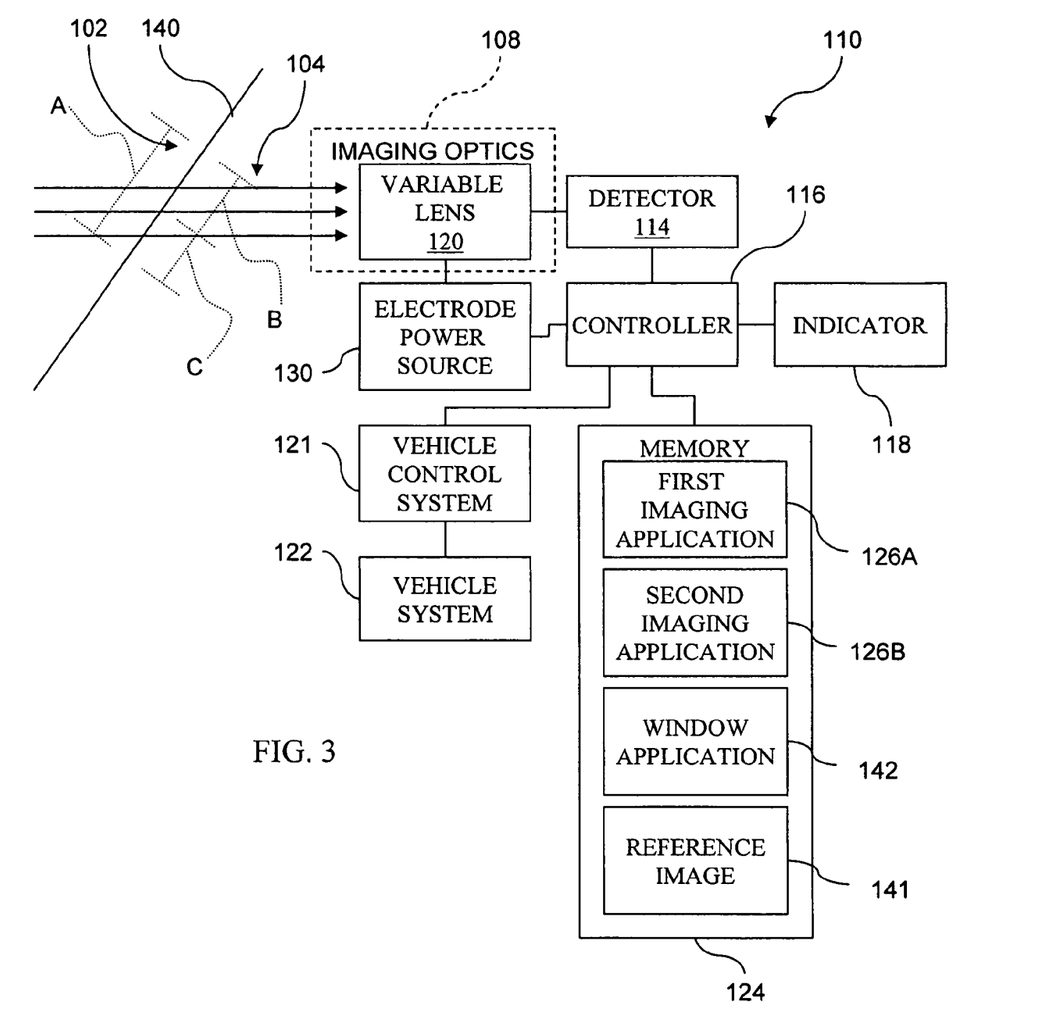
FIG. 3 is a representative view of another exemplary imaging system.

By using variable lens 120, the focal length of imaging optics 108 may be adjusted between imaging object(s) or scene 112 and window 102, such as windshield 140 illustrated in FIG. 3 or another plane of interest. In one embodiment, controller 116 is programmed to compare an image of windshield 140 to one or more reference images 141 of windshield 140 stored in memory 124. Based on that comparison, the condition or optical quality of windshield 140 may be assessed. The data in the image of windshield 140 corresponding to objects 112 will be out of focus and would only affect the relative intensity of the image of windshield 140. This relative intensity may be accounted for by low pass filtering (edge detection) in the image.

In another embodiment, controller 116 is configured to analyze an image of windshield 140 for various image properties, such as the presence of significant higher frequency indicia indicating a non-smooth windshield, artifacts, or varying contrast. Independent of the manner of diagnosing windshield 140 the instructions executed by controller 116 are provided by a window application 142 stored in memory 114. Additional techniques that may be used in the analysis of windshield 140 are generally similar to the techniques use in other imaging applications and may include contrast discrimination, motion, template matching, and other suitable image analysis techniques.

Figure 4:
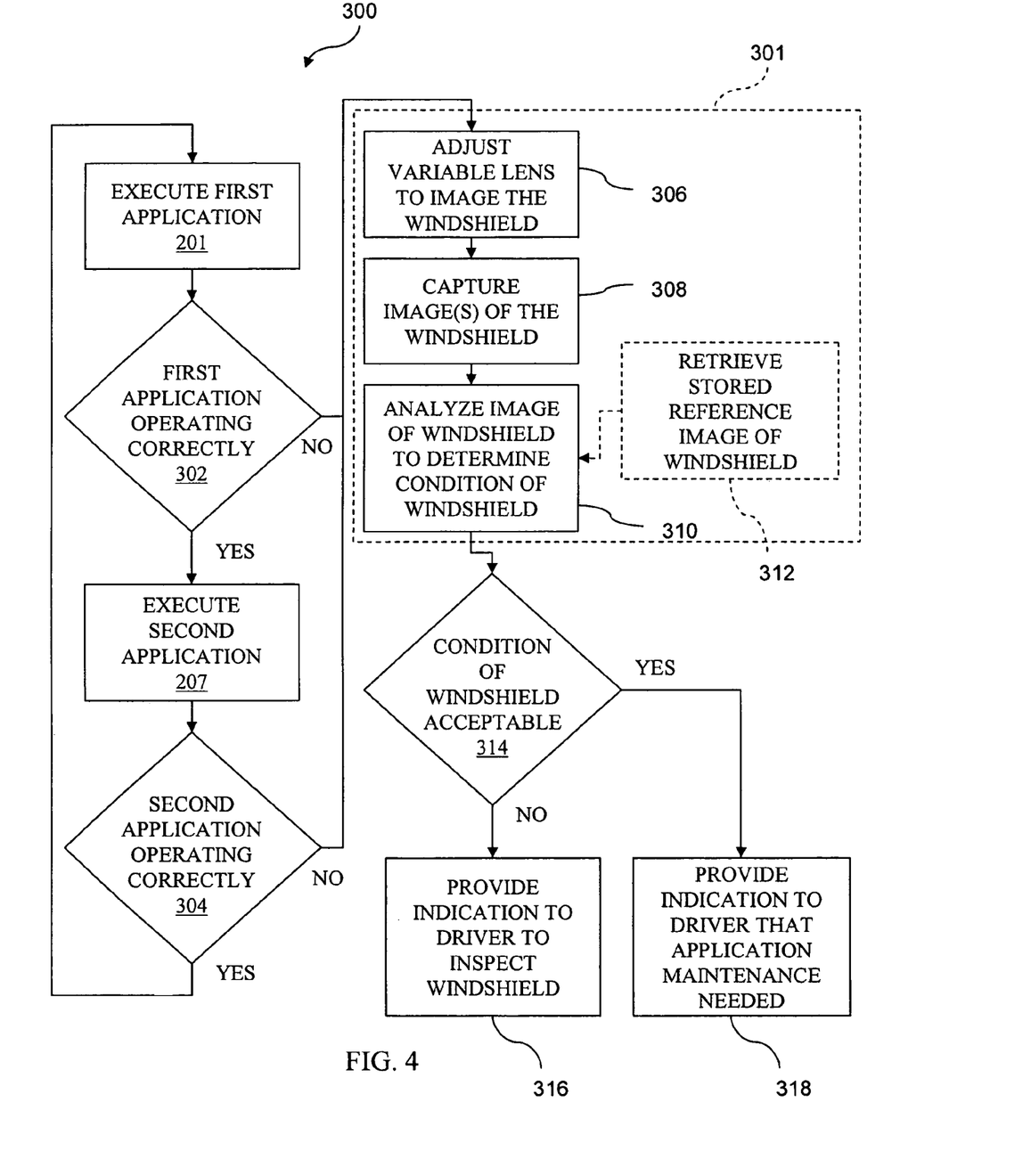
FIG. 4 is a flowchart of an exemplary method to be executed by the imaging system of FIG. 3.

Referring to FIG. 4, an exemplary method 300 of window application 142 is illustrated. Controller 116 executes instructions related to first application 126A, as represented by block 201 which includes blocks 202, 204, and 206 in FIG. 2. Controller 116 determines if first application 126A is operating correctly, as represented by block 302. Examples of incorrect operation include insufficient contrast for a collision warning system, obscured lane markers for a lane detection system, no image present (low light level) for all such systems, and other types of incorrect operation.

If first application 126A is not operating correctly, the condition of windshield 140 is diagnosed to determine if the optical quality of windshield 140 is a potential reason for the failure of the first application 126A. Controller 116 adjusts variable lens 120 so that imaging optics 108 image windshield 140 on detector 114, as represented by block 306. Controller 116 captures one or more images of windshield 140, as represented by block 308. The captured one or more images of windshield 140 are analyzed to determine the condition or optical quality of windshield 140, as represented by block 310. Several techniques of analyzing the one or more images of windshield 140 are discussed above. As illustrated in FIG. 4, in one embodiment, a stored reference image of windshield 140 is retrieved, as represented by block 312, for comparison to the captured one or more images of windshield 140.

In one embodiment, assuming the region of windshield 140 whose condition is relevant to the operation of imaging system 110 is region A, the condition of windshield 140 may need to be determined through multiple iterations because of the slope of windshield 140 relative to the axis of imaging optics 108. For example, variable lens 120 may be adjusted to image sub-region B of windshield 140 and to analyze the condition of sub-region B and then adjusted to image sub-region C and to analyze the condition of sub-region C. In one embodiment, windshield 140 may be imaged and analyzed in strips.

Controller 116 determines if the condition of the windshield 140 is acceptable, as represented by block 314. If the condition of windshield 140 is not acceptable, then controller 116 provides an indication to the driver of vehicle 100 through indicator 118 to inspect windshield 140, as represented by block 316. If the condition of windshield 140 is acceptable, then controller 116 provides an indication to the driver of vehicle 100 through indicator 118 that the respective application 126A, 126B requires maintenance, as represented by block 318.

Figure 5:
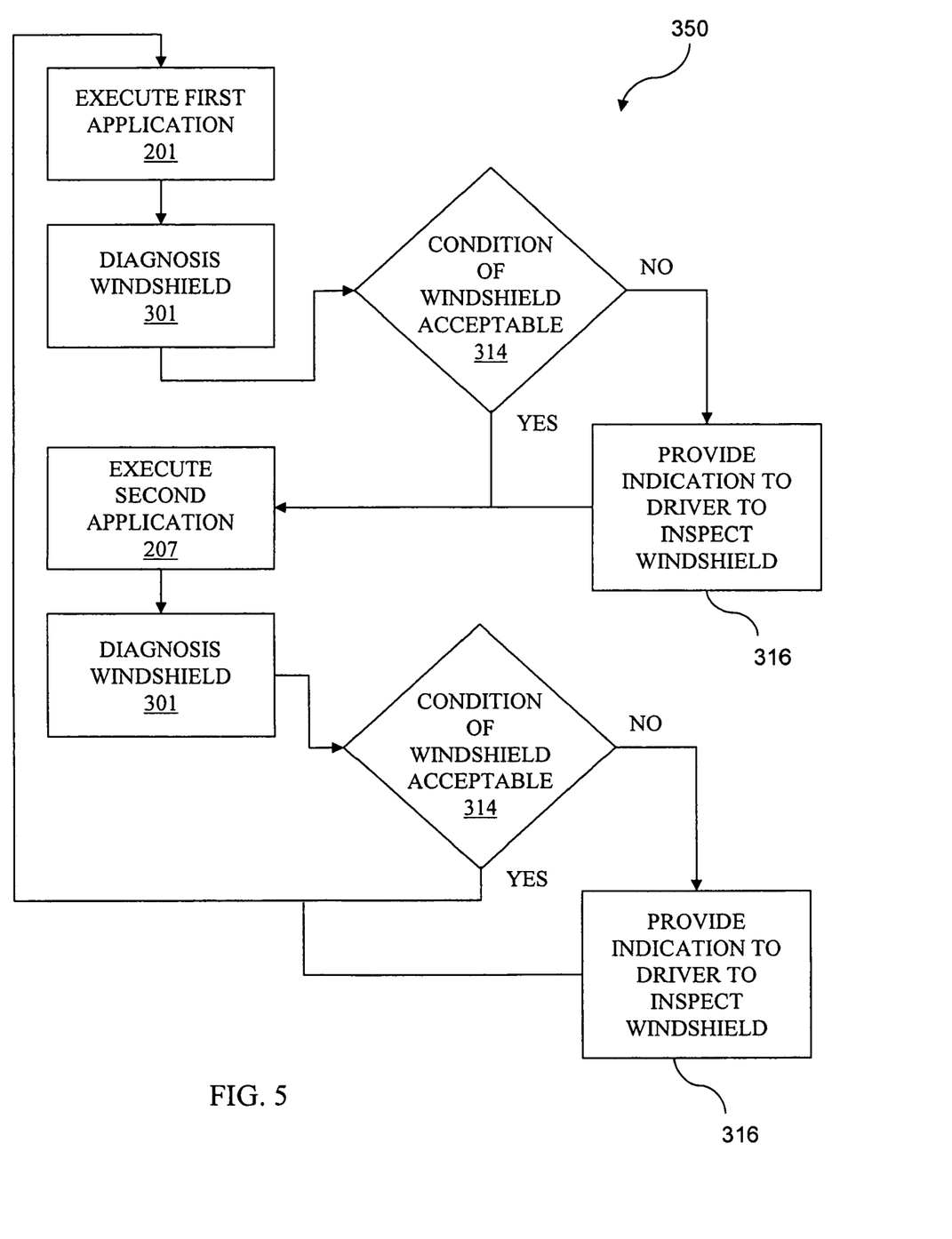
FIG. 5 is a flowchart of another exemplary method to be executed by the imaging system of FIG. 3.

Method 300 of FIG. 4 represents an exemplary method wherein the condition of windshield 140 is checked in response to a failure of a respective imaging application 126A, 126B. Referring to FIG. 5, a method 350 is illustrated which represents an exemplary method wherein the condition of windshield 140 in intermittently checked regardless of the presence or absence of a failure of a respective imaging application 126A, 126B. In one embodiment, the condition of windshield 140 may be checked periodically.

Referring to FIG. 5, controller 116 executes instructions related to first application 126A, as represented by block 201 which includes blocks 202, 204, and 206 in FIG. 2. Controller 116 executes instructions to diagnosis the condition or optical quality of windshield 140, as represented by block 301 which includes blocks 306, 308, 310 and optionally block 312 of FIG. 4. Controller 116 determines if the condition of the windshield 140 is acceptable, as represented by block 314. If the condition of windshield 140 is not acceptable, then controller 116 provides an indication to the driver of vehicle 100 through indicator 118 to inspect windshield 140, as represented by block 316. If the condition of windshield 140 is acceptable, then controller 116 executes instructions related to second application 126B, as represented by block 207 which includes blocks 208, 210, and 212 in FIG. 2. In the illustrated embodiment, controller 116 executes instructions related to second application 126B regardless of whether the condition of windshield 140 is acceptable or not acceptable.

Subsequent to executing instructions related to second application 126B, as represented by block 207, controller 116 again executes instructions to diagnose the condition of windshield 140, as represented by block 301 and as discussed above. In one embodiment, the condition of windshield 140 is only checked subsequent to one of first application 126A or second application 126B. In another embodiment, the condition of windshield 140 is checked independent of the operation of another application. In a further embodiment, the condition of windshield 140 alternates execution by controller 116 with a single other application, such as first application 126A. It should be understood that although the diagnosis of windshield 140 is discussed as being separate from first application 126A or second application 126B, one or more of these functions may be provided in a single software package. Each is discussed separately to highlight the functionality of each and not as a limitation.

Figure 6:
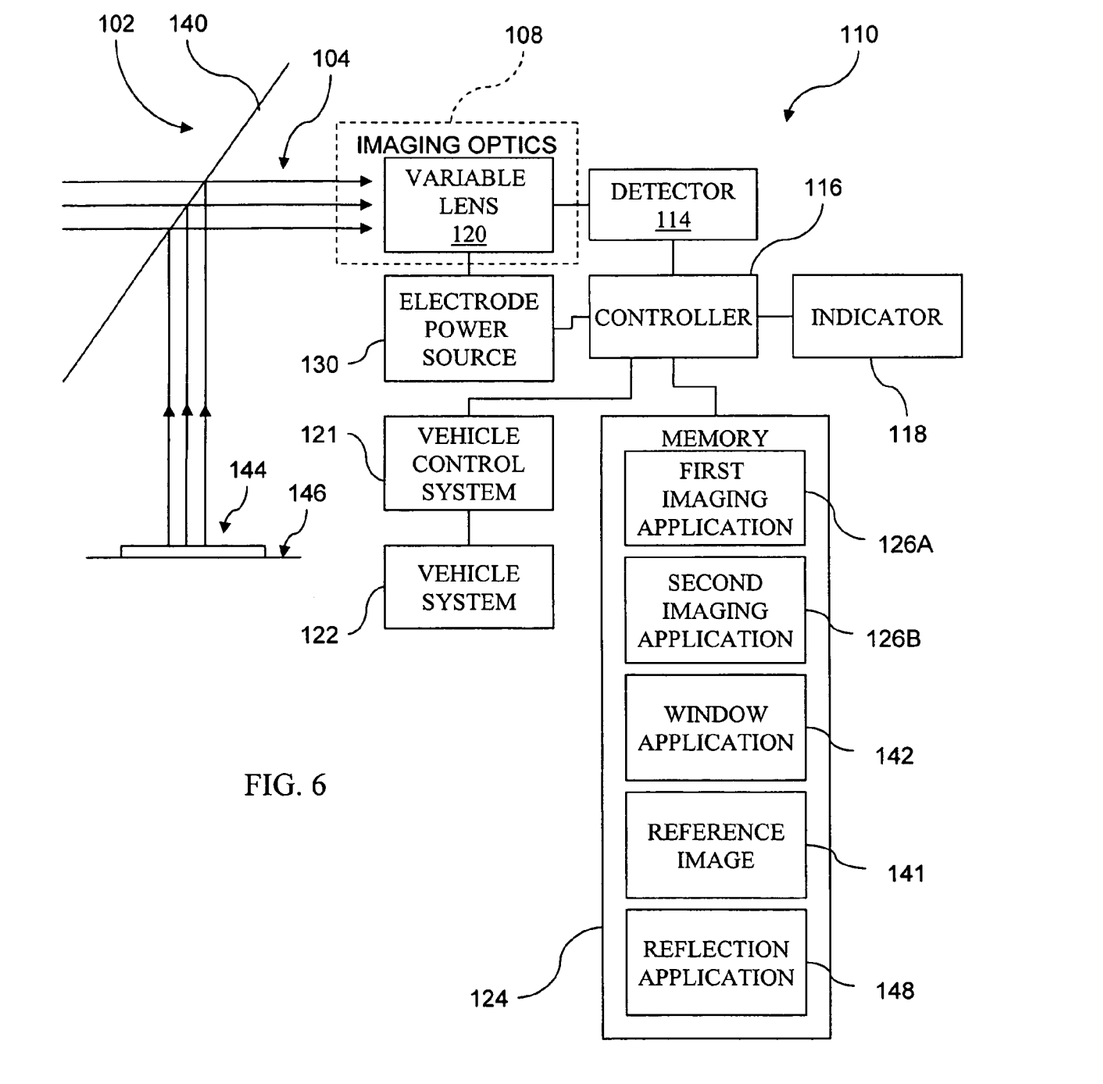
FIG. 6 is a representative view of a further exemplary imaging system.

Variable lens 120 may be used for other applications. For instance, variable lens 120 may be used to adjust the focal length of imaging optics 108 to image an object 144 (see FIG. 6) within vehicle 100, such as papers on a dashboard 146 (see FIG. 6) of vehicle 100. Other objects include passengers, portions of a passenger such as eyes, car seats, or other objects. Referring to FIG. 6, controller 116 is programmed with a reflection application 148 to image object 144 and to alter an image of scene or objects 112 based on the image of object 144. As such, the effect of reflections from object 144 entering imaging optics 108 may be accounted for without a sacrifice of the light entering imaging optics 108 or the need of an additional shield.

Figure 7:
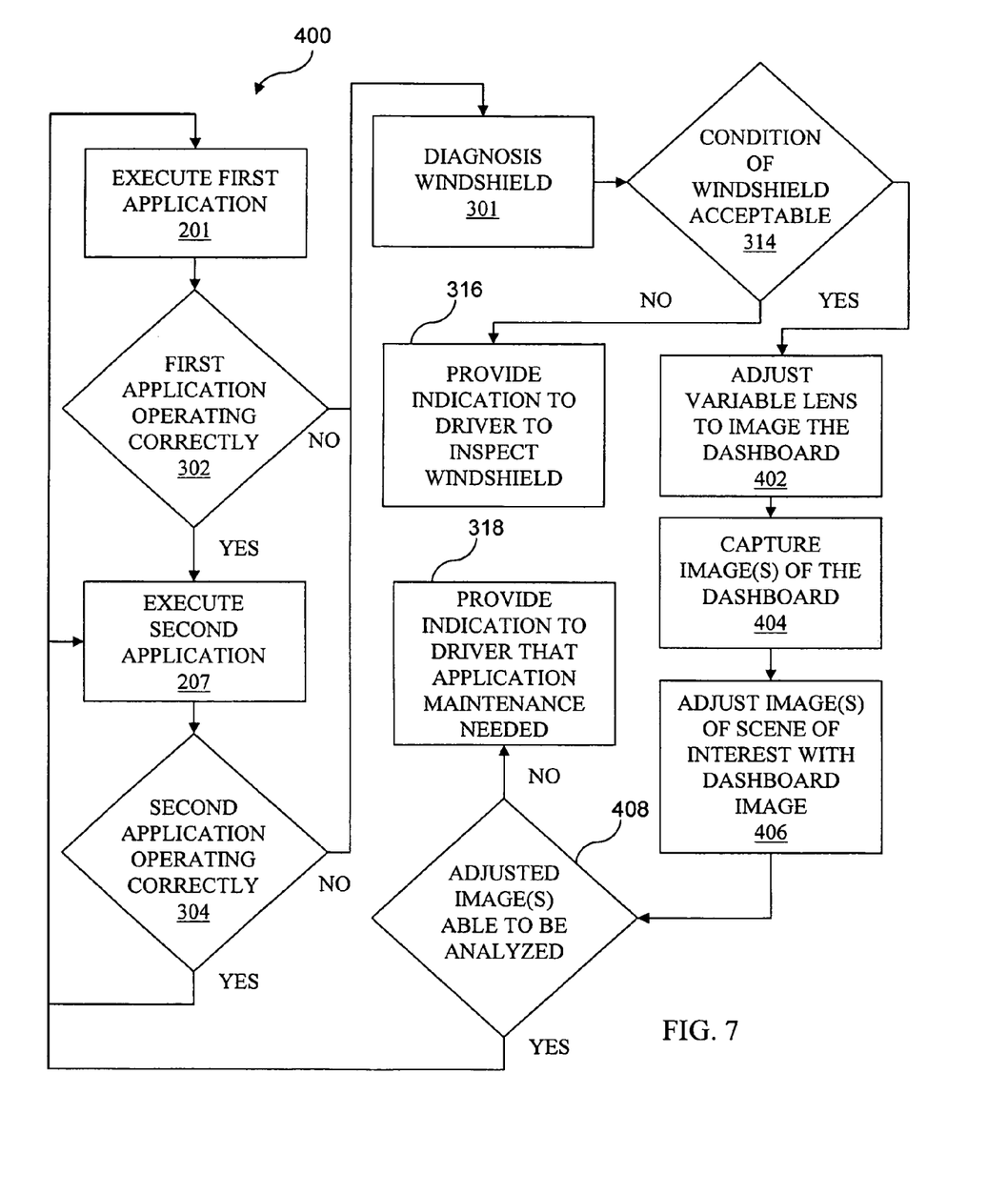
FIG. 7 is a flowchart of an exemplary method to be executed by the imaging system of FIG. 6.

Referring to FIG. 7, controller 116 executes first application 126A, as represented by block 201 and determines whether first application 126A is operating correctly, as represented by block 302. If first application 126A is operating correctly, controller 116 executes a second application 126B, if present, as represented by block 207, or simply continues the execution of first application 126A. If second application 126B is executed, controller 116 determines whether second application 126B is operating correctly, as represented by block 304.

If either of first application 126A or second application 128B is not operating correctly, controller 116 diagnoses windshield 140, as represented by block 301. Controller 116 determines if the condition of windshield 140 is acceptable, as represented by block 314. If the condition of windshield 140 is not acceptable, then controller 116 provides an indication to the driver of vehicle 100 to inspect windshield 140, as represented by block 316. In one embodiment, controller 116 does not diagnosis the condition of windshield 140.

Regardless of whether controller 116 diagnoses the condition of windshield 140, controller 116 adjusts variable lens 120 to image dashboard 146, as represented by block 402. Controller 116 captures one or more images of dashboard 146, as represented by block 404. The ability to periodically focus on dashboard 146 may provide, in one embodiment, the ability to distinguish between object 144 on dashboard 146 inside vehicle 100 and objects 112 outside vehicle 100. Controller 116 adjusts the images of objects or scene 112 captured by controller 116 for the failed first application 126A or second application 126B based on the one or more images captured by controller 116, as represented block 406.

In one embodiment, controller 116 adjusts the images of objects or scene 112 by automatic control of gain and dynamic range compression.

Controller 116 determines if the adjusted images are able to be analyzed by the respective first application 126A or the second application 126B, as represented by block 408. If the adjusted image is not able to be analyzed, controller 116 provides an indication to the driver that the respective application 126A, 126B requires maintenance, as represented by block 318. If the adjusted image is able to be analyzed, controller 116 returns to executing the next of the first application 126A and second application 126B.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. An imaging system for use with a vehicle, the vehicle including a window through which light is transmitted, the imaging system comprising:
   a detector which provides an image of the light transmitted through the window;
   imaging optics including a variable focus lens and having a first configuration wherein an object spaced apart from the vehicle is imaged onto the detector and a second configuration wherein at least a portion of the window is imaged onto the detector; and
   a controller operably coupled to the imaging optics, the controller configured to adjust the imaging optics to place the imaging optics in the first configuration to image the object spaced apart from the vehicle and further configured to adjust the imaging optics to place the imaging optics in the second configuration to image the portion of the window.
   wherein a shape of the variable focus lens is adjusted by the controller, the variable focus lens having a first shape corresponding to the first configuration of the imaging optics and a second shape corresponding to the second configuration of the imaging optics,
   wherein the controller executes instructions to adjust the shape of the variable focus lens to the second shape and to analyze an image of the window to determine a condition of the window,
   wherein the controller further executes instructions to adjust the shape of the variable focus lens to the first shape and to execute an imaging application wherein one or more images of the object spaced apart from the vehicle are analyzed, and
   wherein the controller maintains the variable focus lens in the first shape until the imaging application malfunctions whereat the controller adjusts the shape of the variable focus lens to the second shape to analyze an image of the window to determine a condition of the window.

2. The imaging system of claim 1 wherein a relative placement of the imaging optics remains constant as the imaging optics are adjusted between the first configuration and the second configuration.

3. The imaging system of claim 1, wherein the controller further executes instructions to provide an indication to a driver of the vehicle if the condition of the window is other than acceptable.

4. The imaging system of claim 1, wherein the image of the window is compared to at least one reference image of the window to determine the condition of the window.

5. The imaging system of claim 1, wherein the controller further executes instructions to provide a first indication to a driver of the vehicle if the condition of the window is other than acceptable and to provide a second indication to the driver of the vehicle if the condition of the window is acceptable, the second indication indicating the imaging application requires maintenance.

6. The imaging system of claim 1, wherein the controller further alternates the imaging optics between the first configuration and the second configuration, one or more images of the object being spaced apart from the vehicle being detected by the detector while the imaging optics are in the first configuration and one or more images of the window being detected by the detector while the imaging optics are in the second configuration.

7. The imaging system of claim 1, wherein the imaging optics are placed in a third configuration by the controller to image a second portion of the window.

8. The imaging system of claim 1, wherein the variable focus lens is a fluid lens.

9. The imaging system of claim 8, wherein the shape of the variable focus lens is adjusted by adjusting a voltage applied to a fluid of the variable focus lens.

* * * * *